United States Patent
Kurup

(10) Patent No.: US 7,824,372 B1
(45) Date of Patent: Nov. 2, 2010

(54) SYRINGE GUIDE AND SHIELD FOR USE IN ADMINISTERING OPHTHALMOLOGIC INJECTIONS

(76) Inventor: Shree K. Kurup, 310 W. 4th St. 1404, Winston-Salem, NC (US) 27101

( * ) Notice: Subject to any disclaimer, the term of this patent is extended or adjusted under 35 U.S.C. 154(b) by 0 days.

(21) Appl. No.: 12/454,118

(22) Filed: May 13, 2009

(51) Int. Cl.
*A61M 5/00* (2006.01)
(52) U.S. Cl. ........................ 604/116; 604/117
(58) Field of Classification Search .......... 128/303, 128/305, 858; 351/208; 604/116, 117, 301; 606/107, 166, 172
See application file for complete search history.

(56) References Cited

U.S. PATENT DOCUMENTS

| | | | |
|---|---|---|---|
| 3,961,628 A | 6/1976 | Arnold | |
| 4,573,982 A | 3/1986 | Forbes et al. | |
| 4,688,570 A * | 8/1987 | Kramer et al. | 606/166 |
| 4,981,142 A | 1/1991 | Dachman | |
| 5,314,419 A | 5/1994 | Pelling | |
| 5,382,243 A | 1/1995 | Mulholland | |
| 5,630,827 A | 5/1997 | Vijfvinkel | |
| 5,702,414 A | 12/1997 | Richter et al. | |
| 5,779,696 A * | 7/1998 | Berry et al. | 606/16 |
| 6,299,603 B1 | 10/2001 | Hecker et al. | |
| 7,229,468 B2 * | 6/2007 | Wong et al. | 607/104 |
| 2003/0060763 A1 | 3/2003 | Penfold et al. | |
| 2003/0088241 A1 * | 5/2003 | Hasegawa | 606/28 |
| 2006/0229585 A1 | 10/2006 | Peyman | |
| 2006/0287662 A1 * | 12/2006 | Berry et al. | 606/166 |
| 2008/0065055 A1 * | 3/2008 | Jones et al. | 606/5 |
| 2008/0091224 A1 * | 4/2008 | Griffis et al. | 606/166 |
| 2008/0140103 A1 * | 6/2008 | Gayheart et al. | 606/166 |

* cited by examiner

*Primary Examiner*—Nicholas D Lucchesi
*Assistant Examiner*—Gerald Landry, II
(74) *Attorney, Agent, or Firm*—Robert W Pitts

(57) ABSTRACT

A guide for use in medical procedures involving the eye comprises a shield for protecting portions of a patient's eye, as well as guide apertures through which an instrument, such as a needle can be inserted. The guide is positioned on the patient's eye, and a visible alignment member, such as a central opening will align the guide relative to the cornea, exposed through this opening. The guide apertures would thus be positioned so that penetration of the eye would occur at a site where no damage to the eye, and especially to the lens, could not occur. The guide apertures extend through cylindrical members that will position a syringe and insure proper entry of the needle into the patient's eye.

19 Claims, 5 Drawing Sheets

SYRINGE GUIDE AND SHIELD FOR USE IN ADMINISTERING OPHTHALMOLOGIC INJECTIONS

BACKGROUND OF THE INVENTION

1. Field of the Invention

This invention is related to the administration of a medical procedure to a patient's eye. More specifically this invention is intended for use with an object, such as a needle and syringe that would penetrate the patient's eye for purposes such as the injection of a medicament into the interior of the eye.

2. Description of the Prior Art

Guides or shields are commonly used to insure that medical injections are properly aligned with the portion of the body into which the injection is to be made. These prior art guides and shields must be properly configured for the specific location on the body where the injection is to be made. However, injections of drugs or medicines into a patient's eye have been typically left to the experience and judgment of an experienced medical professional. It has been suggested that a covering or shield should be used to prevent damage to sensitive parts of the eye when these injections are made. For example, it is important to avoid damage to the lens when an injection is made to the frontal portion of the eye. One suggestion has been to use a plaque that has an inner surface that conforms to the exterior of the eye. A needle could then be inserted through one of several holes through a relatively flat plaque. This prior device is believed to have several practical problems. For instance there appears to be no positive provision for aligning the plaque with the eye, and alignment remains a matter of judgment. Also the plaque is rather thin, and it would appear to be a needle could be inserted at an angle relative to the spherical surface of the eye, and damage could be done to the eye and especially to the lens.

SUMMARY OF THE INVENTION

The instant invention is intended for use with medical instruments that will penetrate the eye. The preferred embodiments are especially intended for use with syringes and needles used to inject drugs, medicines, medicaments or fluids into the eye. Medications for treating cancer or macular degeneration need to be injected directly into a patient's eye, but damage to the eye, and especially to the lens, must be avoided during these medical procedures. Although experienced health care professionals can administer such care without injuring the patient's eye, the use of a shield or guide that would reduce any chance of damage is desirable for use by less experienced personnel or to prevent accidents that can occur even when highly skilled and experienced heath care professionals administer such care.

A device for improving care in this manner can comprise a guide for use with a needle to prevent damage to a patient's eye when the needle is injected into the patient's eye. This guide can include a shield having an inner contour that conforms to the exterior of the patient's eye, when the shield is positioned on the front of the patient's eye. A guide aperture would extend though the shield. The guide aperture would be configured so that the needle can be inserted through the guide aperture and into the patient's eye. A visibly alignable alignment member would be provided on the shield. The alignment member would be configured so that the shield can be visibly aligned with the cornea of the patient's eye and the guide aperture can be positioned relative to the eye so that the needle will not damage the patient's eye when the alignment member is visibly aligned with the cornea.

Such a guide would position a syringe relative to a patient's eye. This guide would include a base having a lower surface configured to rest on the eye. At least one cylindrical member would extend from the base and have a height greater than the thickness of the base. This cylindrical member would include a guide aperture extending though the cylindrical member and through the base. An interior surface on the cylindrical member forms an entry into the guide aperture so that a needle on the syringe can be inserted into the guide aperture. The interior surface would be configured so that the syringe can be positioned in abutting relationship to the interior surface to control the depth of insertion of the needle into the eye.

This guide for use with a syringe and syringe needle can employ a shield positionable on a frontal surface of the eye relative to the cornea of the eye. The guide aperture extending through the shield would permit the needle to enter the guide aperture only in a position in which the lens of the eye is shielded by the shield from damage by the needle when inserted through the guide aperture. At least one cylindrical member would extend outward from the shield, with the guide aperture extending through the cylindrical member and the shield. The cylindrical member includes a support surface engagable with the syringe so that the needle can only be inserted into the eye to a prescribed distance.

DETAILED DESCRIPTION OF THE PREFERRED EMBODIMENTS

Figure 6:
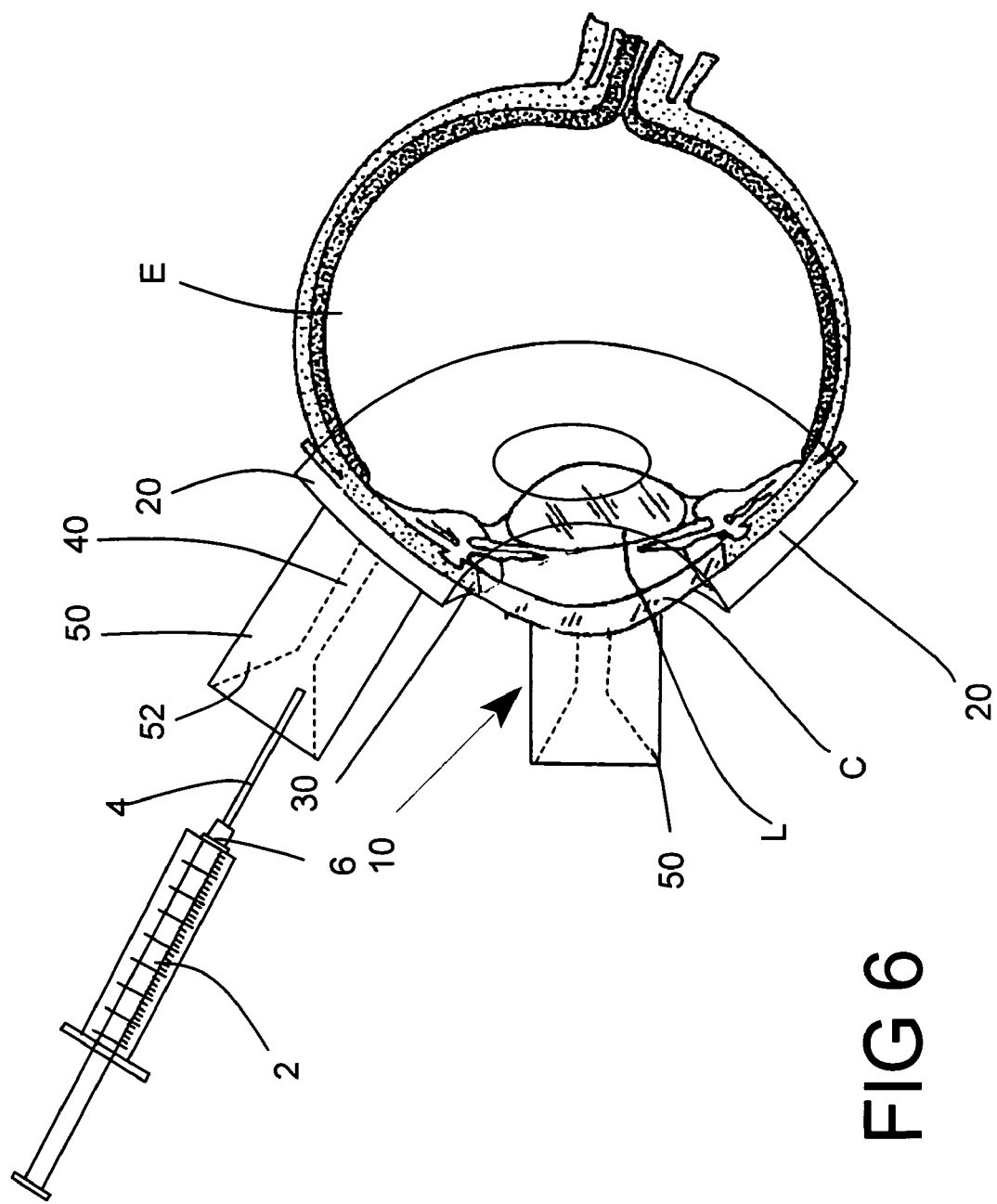
FIG. 6 is a view shown the use of the guide to align the needle on a syringe that is to be used to inject a fluid into the frontal portion of the patient's eye.
Figure 7:
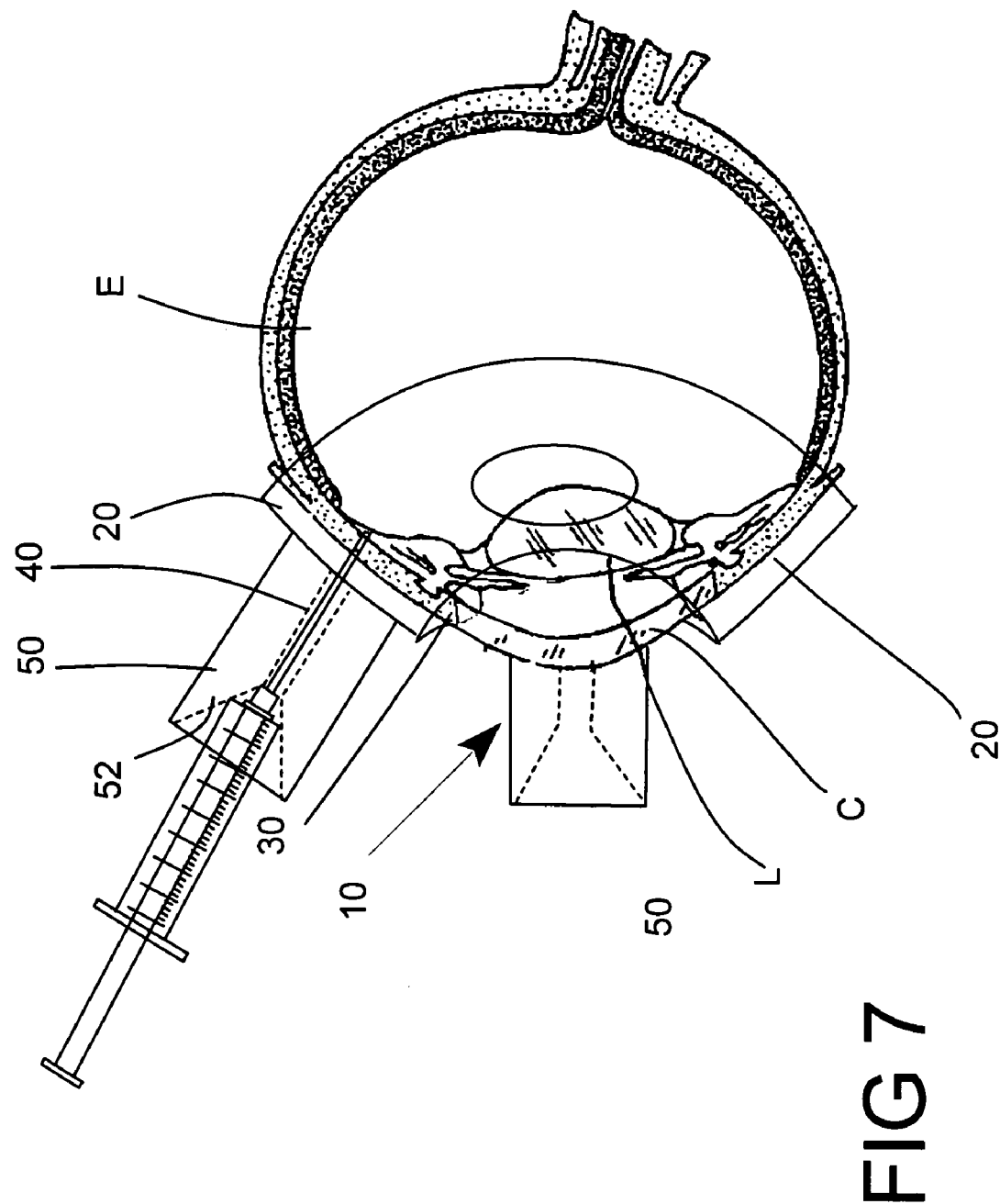
FIG. 7 is a view similar to FIG. 6 showing the position of the syringe and the needle when a fluid is injected into the interior of the patient's eye.
Figure 8:
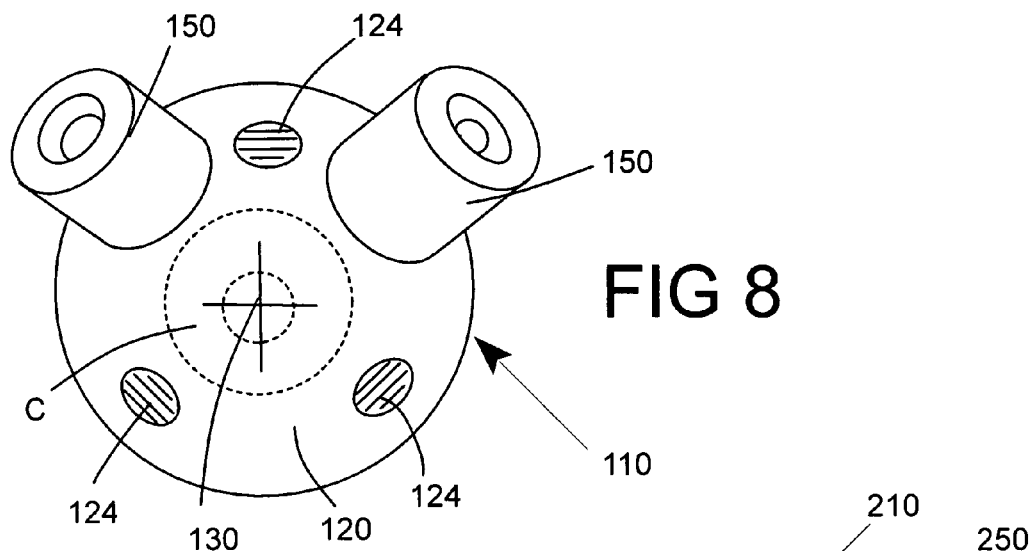
FIG. 8 is an alternative embodiment of a guide in which a surface indicia, such as a cross is used to align the guide with the patient's cornea.
Figure 9:
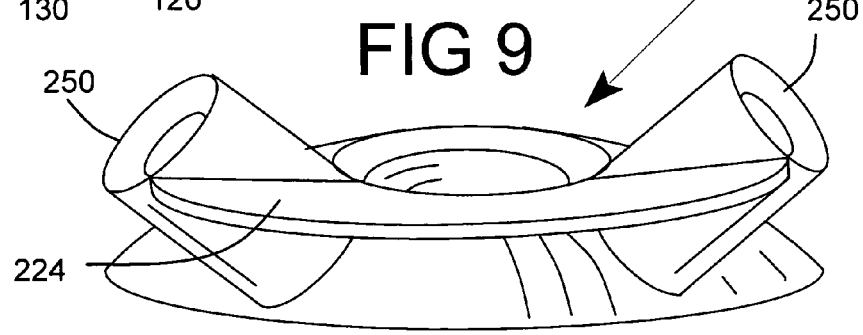
FIG. 9 is another alternative embodiment of a guide having a different gripping member to align the guide.
Figure 10:
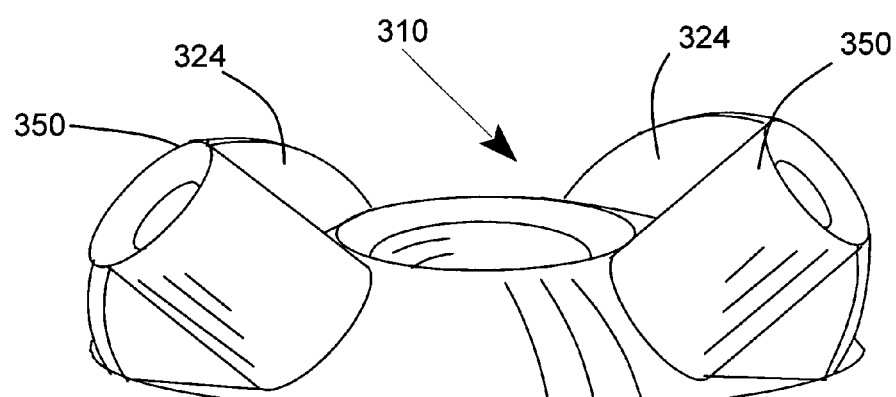
FIG. 10 is still another alternative embodiment of a guide using a different gripping member.

The preferred embodiment of this invention is depicted in FIGS. 1-7. Alternative embodiments, demonstrating that different subcomponents can be used to practice the invention, are shown in FIG. 8-10.

Figure 1:
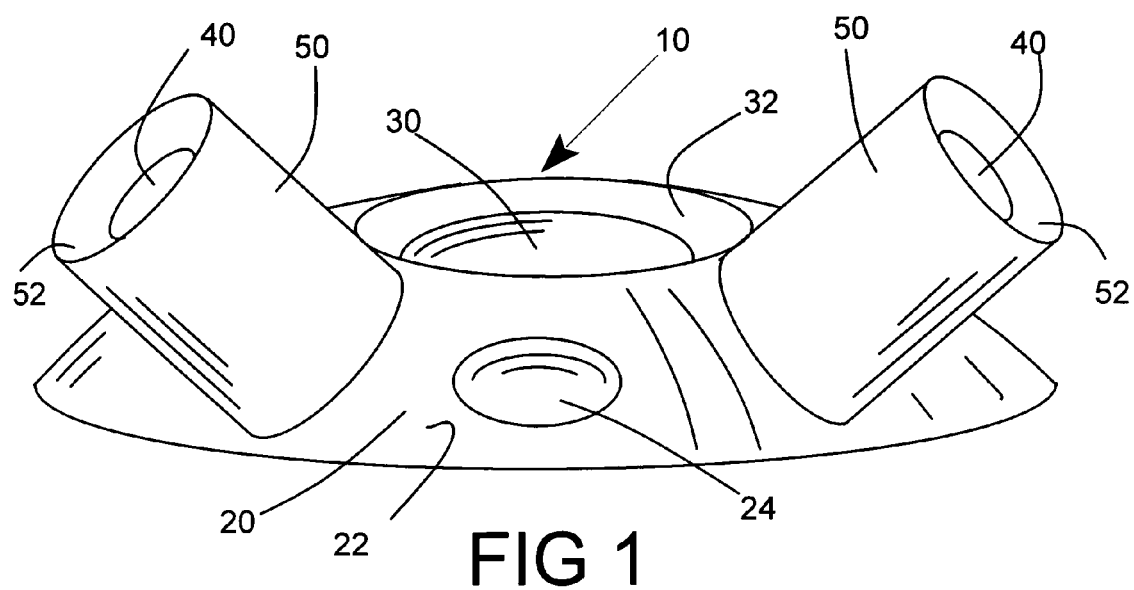
FIG. 1 is a view of the opthalmologic guide for use to prevent damage to the eye when an injection or incision is made into the frontal portion of the eye.
Figure 3:
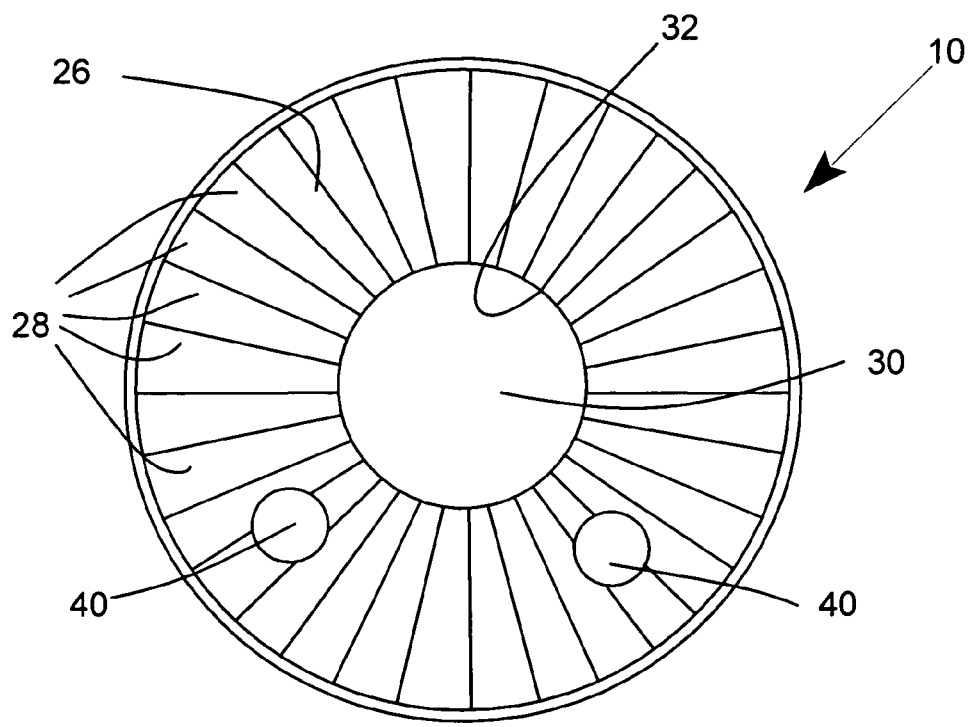
FIG. 3 is a view of the interior surface of the guide shown in FIG. 1.

The guide 10 of FIG. 1 employs a semispherical shield 20 that will cover a portion of the front of a patient's eye E. The guide 10 includes two cylindrical members 50 extending beyond the exterior surface 22 of the shield 20. Each of these cylindrical members 50 has a guide aperture 40 that extends not only through the cylindrical member 50, but also through the shield 20, as shown in FIG. 3. A syringe needle 4 can be aligned with and inserted through this guide aperture 40 when the guide 10 is properly positioned relative to the eye so that the needle 4 will be inserted only at the proper location on the patient's eye.

The semispherical shield 20 will conform to a frontal portion of the eye. The outer diameter of the shield 20 can be on the order of four (4) cm to six (6) cm, depending upon the size of the eye, so that the shield can be inserted on the patient's eye without undue or uncomfortable interference with the patient's eyelid. A central visual alignment opening 30 serves to align the guide 10 relative to the cornea C of the patient's eye. In the preferred embodiment, the shape of the alignment opening 30 will generally conform to the shape of the cornea C, so that when the cornea is visible through the opening 30, the health care professional using the guide 10 will be assured that the guide aperture 40, though which the needle 4 will be inserted, is in the proper location. Although the alignment opening 30 will generally conform a normal cornea C, it should be understood that it is not necessary for the opening 30 to have exactly the same shape and size as the cornea for the specific patient with whom the guide 10 is being used. It is sufficient if the heath care professional can see that the visual alignment opening 30 is centered relative to the patient's cornea, provided that the spacing between the guide aperture 40 and the edge 32 of the alignment opening 30 is sufficient to insure that a needle 4 inserted through the guide aperture 40 will not damage the eye. In the preferred embodiment of this invention, this spacing must be sufficient to insure that the needle 4 will not damage the lens L behind the cornea C.

In the preferred embodiment of this invention, two cylindrical members 50 extend upward from the shield 20 between the central alignment opening 30 and outer periphery of the shield 20. Preferably, each of these cylindrical members will extend perpendicular to the exterior surface 22 of the base or shield 20, so that the cylindrical members 50 will extend generally radially relative to the patient's eye when the guide 10 is properly positioned. Although only one cylindrical member 50 will be used for a single procedure, the inclusion of a second cylindrical member 50 can give the health care professional an option as to which site the injection is to be made. In the preferred embodiment, the height of the cylindrical member 50, measured from the top or distal end to the exterior surface of the shield or base 20 can be three quarters (¾) of an inch, which will be suitable for use with a 1 inch needle. This height will be sufficient to insure that the needle 4 will be inserted only to the proper depth. For an eye having a diameter of 22 mm., the insertion depth for the needle 4 should be between one and two (1 and 2) mm. The two cylindrical members 50 are located on the same half of the shield 20. Normally the guide 10 would be used with a patient in a reclining position and the guide 10 would be oriented so that the health care professional would administer treatment to the lower portion of the eye, which would be most easily accessible with the patient in this reclining position.

A tapered surface 52 extends inwardly from the upper or distal end of each cylindrical member 50, and merges with the guide aperture 40, which is concentric with the axis of the corresponding cylindrical member 50. The tapered surface 52 extends completely around the upper edge of guide aperture 40. The tapered surface 52 will serve several purposes. First, tapered surface 52 will serve as a target that is larger than the guide aperture 40, to direct the needle 4 into the guide aperture 40, as shown in FIG. 6. The tapered surface 52 and the guide aperture will act to funnel the needle 4 into its proper orientation with the desired location on the patient's eye E. The tapered surface 52 will also serve as a seat that will engage the foremost end of the syringe body 6 so that the syringe 2 will be seated relative to the guide 10 as well as relative to the patient's eye E as shown in FIG. 7. The seat 52 will also serve as a reaction surface, holding the syringe body in place, as fluid is injected through the needle 4, and will more evenly distribute this force over the patient's eye E. It should be understood that the simple taper of surface 52, depicted herein, is not essential, and other shapes, more nearly compatible to the foremost end of the syringe body may be employed to further limit the angle of the syringe 2 and the needle 4 relative to the patient's eye E.

Employment of two cylindrical members 50 instead of one provides several advantages. First this will define optional sights for penetrating the eye. Alternatively, the two cylindrical members 50 will allow the health care professional to use either the left or right hand to position the guide 10 and manipulate the syringe 2. Although normally the two cylindrical members 50 would be identical, it would also be possible to employ different sizes so that the same guide 10 could be employed with different needles and for different procedures.

Although the diameter of each guide aperture 40 must be larger than the outer diameter of the needle 4 so that the needle can be inserted through the guide 10, a reasonably close fit is desirable. In the preferred embodiment, the diameter of guide aperture 40 is 2.5 mm for use with a one-half (½) inch needle having an outer diameter of 1-2 mm. Of course other sizes can be employed. Since most of the length of the needle 4 will extend through the guide aperture 40, the angle of insertion of the needle 4 into the frontal region of the patient's eye will be controlled by the orientation of the guide aperture 40. When the guide 10 is properly placed on the patient's eye, the needle 4 will enter radially and will not be cocked or angled relative to the frontal surface of the eye. Thus if the position of the guide aperture 40 is correct, the needle 4 cannot enter at an angle which would damage sensitive portions of the eye, such as the lens L. Visual alignment of the guide 10 with the patient's cornea C will fix the guide 10 in the proper position for penetration by the needle 4, or other instrument with which this guide or a modified guide might be used.

Figure 4:
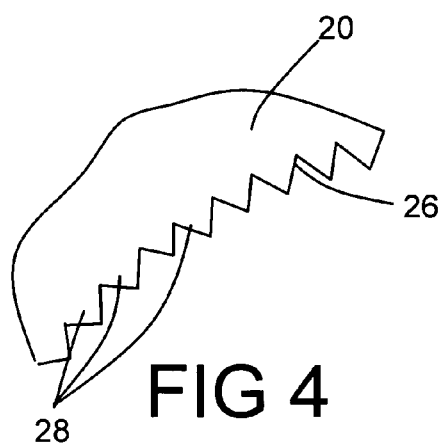
FIG. 4 is an enlarged view of a portion of the interior surface of the guide, showing the uneven or serrated interior surface.
Figure 5:
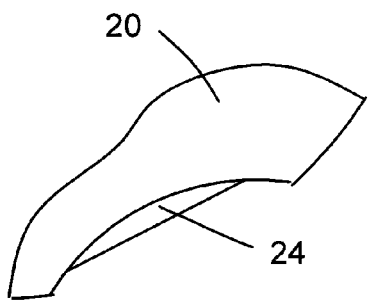
FIG. 5 is an enlarged view of a portion of the exterior surface of the guide, showing gripping sections, which will allow the care giver to position the guide using his or her finger or fingers.
Figure 2:
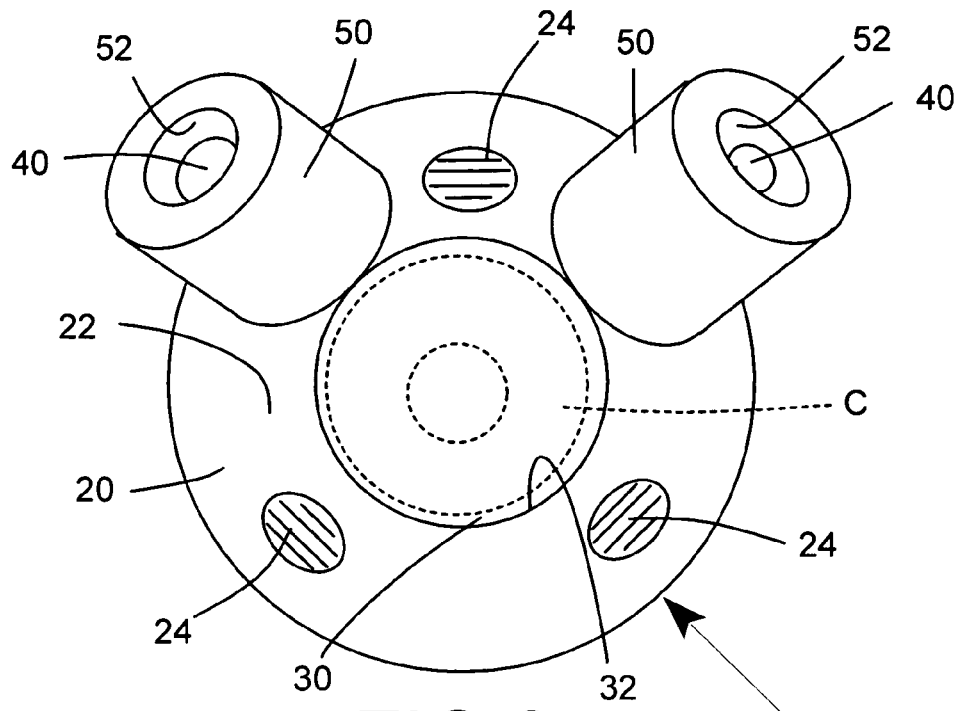
FIG. 2 is a view of the exterior of frontal face of the guide shown in FIG. 1.

The interior surface 26 of the shield 20 will lie against the frontal surface of the patient's eye E. To insure that the guide 10 does not slip relative to the eye E, after the alignment opening 30 has been aligned with the cornea C, the interior surface 26 is uneven. As shown in FIGS. 3 and 4, this interior surface 26 can contain serrations 28. Although these serrations 28 may have somewhat sharp edges, the outer frontal surface of patient's eye surrounding the cornea C is not sensitive to these serrated edges 28, provided of course that the serrations do not cut or otherwise damage the eye tissue. Once the guide 10 is aligned with the cornea C, the health care professional can apply light pressure to the shield 20 to hold the guide 10 in place so that the needle 4 can be inserted through the guide aperture 40 and into the patient's eye E. As seen in FIGS. 2 and 3, depressions or gripping surfaces 24 can be formed on the exterior shield surface 22. In this embodiment, these gripping surfaces 24 will provide space for finger pressure to be applied so that the health care professional can use one hand to hold the guide 10 in place, and can align and insert the needle 4 into the guide aperture 40 and then inject a fluid or medicament into the eye without damaging the lens L or other structures of the eye.

The guide 10 can be fabricated as a one piece item. Normally the guide 10 would be injection molded from a suitable thermoplastic. It should be understood, however that this guide could be fabricated in whole or in part by other means, such as machining. For example, the guide apertures might be drilled as part of a secondary operation for those situations in which closer tolerances, than could be obtained by molding, were desired. The guide 10 could also be fabricated as a throw away for only a single use or it could comprise a permanent instrument suitable for continued use.

The preferred embodiment of FIGS. 1-7 is especially suited for injecting medicines in the eye, but the structure disclosed in that embodiment may be modified, without adversely compromising care. Examples of such modifications that could require additional consideration are shown in FIGS. 8-10. FIG. 8 shows an example in which the guide 110 can be aligned with the cornea C by alternate means. In this embodiment, the entire shield 112 would be fabricated from a transparent plastic. Instead of the opening employed with the previous embodiment, a visible indicia, such as cross hairs 130 would be employed to align the guide 110. The cross hairs 130 would be aligned with the center of the cornea C and the device could still be employed in substantially the same manner. If the shield 120 is molded from a transparent plastic, it would be desirable to also mold the cylindrical members 150 of the same material as part of the same one piece structure in which gripping sections 124 can be dispersed around the shield 120.

FIG. 9 shows an embodiment of a guide 210 in which a gripping ledge 224 would extend between two cylindrical members 250. The health care professional could simply grip the ledge 224 to properly position the guide 210 relative to the patient's eye. FIG. 10 shows an embodiment of the guide 310 in which ribs 324 integral with the cylindrical members 350 could function as gripping members.

These alternative structures are merely intended to show some examples of modifications to the preferred embodiment of the invention that would be apparent to those of ordinary skill in the art. Other modification could also be made without departing from the invention as defined in the following claims.

I claim:

1. A guide for use with a needle to prevent damage to a patient's eye when the needle is injected into the patient's eye, the guide comprising:
   a shield having an inner contour that conforms to the exterior of the patient's eye, at least partially beyond its cornea, when the shield is positioned on the front of the patient's eye;
   a guide aperture extending through the shield, the guide aperture being configured so that the needle can be inserted through the guide aperture and into the patient's eye, wherein the guide aperture extends through a cylindrical member extending beyond an exterior surface of the shield to provide an internal guiding surface having a length greater than the thickness of portions of the shield spaced from the cylindrical member; and
   a visibly alignable alignment member on the shield, the alignment member being configured so that the shield can be visibly aligned relative to the cornea of the patient's eye and the guide aperture can be positioned relative to the eye so that the needle will not damage the patient's eye when the alignment member is visibly aligned with the cornea.

2. The guide of claim 1 wherein the alignment member comprises an opening through which the cornea of the patient's eye is visible.

3. The guide of claim 2 wherein the opening is large enough so that the entire cornea is visible through the opening.

4. The guide of claim 3 wherein the opening conforms to the shape of the cornea of the patient's eye.

5. The guide of claim 2 wherein the opening is centrally located in the guide.

6. The guide of claim 1 wherein the alignment member comprises a visible indicia on the shield.

7. The guide of claim 1 wherein the cylindrical member includes a surface engagable with a syringe body when the needle is inserted through the guide aperture.

8. The guide of claim 1 including multiple guide apertures and multiple corresponding cylindrical members.

9. The guide of claim 1 wherein the shield has a semispherical shape generally conformable to portions of the patient's eye adjacent to the cornea.

10. The guide of claim 1 wherein the shield has an uneven interior surface enagable with the patient's eye to prevent slippage of the shield once positioned with the alignment member visibly aligned with the cornea.

11. The guide of claim 10 wherein the uneven interior surface comprises a serrated lower surface.

12. The guide of claim 10 wherein the shield includes a gripping surface on the exterior of the shield, which can be gripped by the user to keep the guide properly positioned relative to the lens of the patient's eye.

13. The guide of claim 12 wherein the gripping surface comprises a depression that can be engaged by the finger of the person injecting the needle into the patient's eye.

14. The guide of claim 12 wherein the shield has a circular periphery so that the guide can be positioned beneath the patient's eyelid.

15. A guide for positioning a syringe relative to a patient's so that injections into the eye can be made without damaging the eye, the guide comprising:
   a base having an interior surface configured to rest on the eye at least partially beyond its cornea;
   a cylindrical member extending from the base and having a height greater than the thickness of the base, the cylindrical member including a guide aperture extending though the cylindrical member and through the base; a surface within the cylindrical member forming an entry into the guide aperture so that a needle on the syringe can be inserted into the guide aperture, the interior surface being configured so that the syringe can be positioned in abutting relationship to the interior surface to control the depth of insertion of the needle into the eye.

16. The guide of claim 15 wherein the base is alignable relative to the cornea of the eye so that the guide aperture can be aligned with an intended injection site on the eye.

17. The guide of claim 15 wherein the cylindrical member comprises a right circular cylinder.

18. A guide for use with a syringe and syringe needle to prevent damage to the lens of a patient's eye when the needle is injected into the patient's eye, the guide comprising:
   a shield positionable on a frontal surface of the eye relative to the cornea of the eye, the shield being larger than the cornea of the eye to be at least partially positionable on a portion of the frontal surface of the eye extending beyond the cornea;
   a guide aperture extending through the shield so that the needle can enter the guide aperture only in a position in which the lens of the eye is shielded by the shield from damage by the needle when inserted through the guide aperture; and
   a cylindrical member extending outward from the shield, with the guide aperture extending through the cylindrical member and the shield, the cylindrical member including a support surface engagable with the syringe so that the needle can only be inserted into the eye to a prescribed distance.

19. The guide of claim 18 wherein the cylindrical member extends beyond the shield so that the distance between the frontal surface of the eye and the support surface is greater than the thickness of the shield.

* * * * *